United States Patent [19]

Sauter et al.

[11] 4,189,486
[45] Feb. 19, 1980

[54] 1-(3-PYRIDYL)-2,2,2-TRIHALOETHYL COMPOUNDS

[75] Inventors: Fritz Sauter, Vienna, Austria; Otto Eberle, Ottobrunn, Fed. Rep. of Germany; Beate Süss; Rudolf Weissgerber, both of Munich, Fed. Rep. of Germany

[73] Assignee: Consortium für Elektrochemische Industrie GmbH, Munich, Fed. Rep. of Germany

[21] Appl. No.: 863,980

[22] Filed: Dec. 23, 1977

[30] Foreign Application Priority Data

Dec. 28, 1976 [DE] Fed. Rep. of Germany ....... 2659117

[51] Int. Cl.$^2$ ..................... C07D 213/30; A01N 9/22
[52] U.S. Cl. .................................. 424/263; 546/344; 546/343
[58] Field of Search ............... 260/297 R, 290 HL; 546/344; 424/263

[56] References Cited

U.S. PATENT DOCUMENTS

| | | | |
|---|---|---|---|
| 3,396,224 | 8/1968 | Heyningen | 546/344 |
| 3,400,126 | 9/1968 | Brust et al. | 546/344 |
| 3,652,575 | 3/1972 | Hutton et al. | 546/344 |

*Primary Examiner*—Alan L. Rotman
*Attorney, Agent, or Firm*—Allison C. Collard; Thomas M. Galgano

[57] ABSTRACT

1-(3-Pyridyl)-2,2,2-trihaloethyl compounds of the general formula I

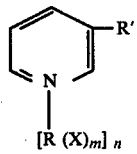

[R (X)$_m$]$_n$ in which n is 0 or 1, R represents oxygen, hydrogen or an organic radical having at the most 12 C-atoms, m is 0 when R is oxygen, m is ½ or 1 when R is hydrogen or an aliphatic or aralkyl radical, and X represents a negative ion, R' represents a radical of the general formula II

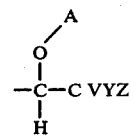

wherein V, Y, Z represent chlorine or bromine and may be identical or different, but are preferably identical; A represents hydrogen or a radical of the general formula III

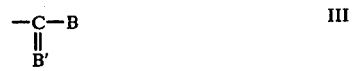

wherein B' is oxygen or sulphur, and B stands for an organic radical having up to 12 C atoms, or for an amino group of the general formula IV

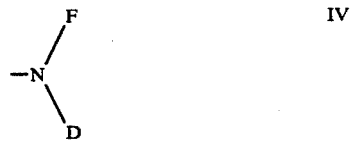

wherein F and D are identical or different, and represent hydrogen or organic radicals having at most 12 C-atoms; A may further be a sulphonyl group of the general formula —SO$_2$—B, in which B has the same meaning as in formula III. The invention also relates to a process of making the compounds, which are effective ingredients of fungicides and seed-dressing agents.

15 Claims, No Drawings

1-(3-PYRIDYL)-2,2,2-TRIHALOETHYL COMPOUNDS

The invention relates to 1-(3-pyridyl)-2,2,2-trihaloethyl compounds of the general empirical formula I

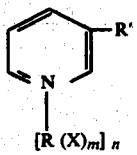

in which n is 0 or 1, R represents an oxygen atom, a hydrogen atom or an aliphatic radical having from 1 to 12 C-atoms, or an aralkyl radical having from 7 to 12 C-atoms, m is 0 when R is an oxygen atom, m is ½ or 1 when R is a hydrogen atom or an aliphatic or aralkyl radical, and X represents a negative ion; the radical R' represents a radical of the general formula II

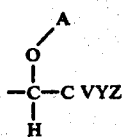

wherein V, Y and Z represent a chlorine or bromine atom, which may be identical or different, but are preferably identical, A represents a hdyrogen atom or a radical of the general formula III

in which B' is an oxygen atom or a sulphur atom and B stands for an aliphatic radical having from 1 to 10 C-atoms, or an optionally substituted aromatic radical, or an optionally substituted aralkyl racidal having from 7 to 12 C-atoms, or for an amino group of the general formula IV

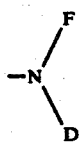

in which F and D are identical or different, and represent hydrogen atoms, aliphatic radicals having from 1 to 10 C-atoms, or aromatic radicals or aralkyl radicals having from 7 to 12 C-atoms; A may further be a sulphonyl group of the general formula —SO$_2$—B, in which B has the same meaning as in formula III, and to a process for making the same.

Suitable examples of the compounds of the invention are in particular:

Compounds as defined in the above formulas, wherein in formula I, n is O and, in formula II, A is H.

Furthermore, compounds wherein in formula I, R represents an oxygen atom, m is O, and n is 1, and also, in formula II, A is preferably H.

Also, compounds wherein in formula I, R is H or an aliphatic radical having from 1 to 12 C-atoms, or an optionally substituted aralkyl radical having from 7 to 12 C-atoms, and, in formula II, A is preferably H.

Furthermore, compounds wherein in formula I, n is preferably O, in formula II, A has the meaning given by formula III, in which B' represents oxygen or sulphur, preferably oxygen, and B is an aliphatic radical having from 1 to 10 C-atoms, or is an optionally substituted aromatic radical.

Equally suitable are compounds wherein in formula I, n is preferably O, in formula II, A has the meaning given by formula III, in which B' may be oxygen or sulphur, preferably oxygen, and B has the meaning given by formula IV.

Excellent compounds are further those wherein in formula I, n is O, also in formula I, R' is a radical of the general formula II, in which V, Y and Z are identical and represent Cl or Br, A represents preferably H or has the meaning given by formula III, in which B represents an optionally substituted aromatic radical, and B' may represent an oxygen atom or A may be a sulophonyll group of the general formula —SO$_2$—B, in which B represents an aliphatic radical having from 1 to 10 C-atoms, or an optionally substituted aromatic radical.

Successful types of compounds of the invention are also compounds which fulfill the conditions mentioned in the preceding paragraph, but instead of n being O, n is 1 and R is oxygen or hydrogen, in which when R is hydrogen, X is a negative ion and m=½ or 1, and in which, when R is oxygen, m is O.

Individual examples from the class of the compounds of this invention are listed in the following Table 1.

TABLE I

| Compound | R | X | R' | mp (°C.) | |
|---|---|---|---|---|---|
| 1 | — | — | —CHOH—CCl$_3$ | 141 | |
| 2 | O$^\ominus$ | — | —CHOH—CCl$_3$ | 171 | |
| 3 | — | — | —CHOH—CBr$_3$ | 163 | |
| 4 | — | — | —CH(O—CO—C$_6$H$_5$)—CCl$_3$ | 65 | |
| 5 | H$^\oplus$ | Cl$^\ominus$ | —CHOH—CCl$_3$ | 180-190 | (Decomposition) |

TABLE I-continued

| Compound | R | X | R' | mp (°C.) |
|---|---|---|---|---|
| 6 | — | — | —CH(O—SO₂—CH₃)—CCl₃ | 113 |
| 7 | —CH₃⊕ | I⊖ | —CHOH—CCl₃ | 193 |
| 8 | — | — | —CH(O—CO—CH₃)—CCl₃ | 87 |
| 9 | — | — | —CH(O—CO—C₂H₅)—CCl₃ | 35 |
| 10 | — | — | —CH(O—CO—N(C₂H₅)₂)—CCl₃ | 62 |
| 11 | — | — | —CH(O—CO—NH—C₆H₅)—CCl₃ | 146 |
| 12 | — | — | —CH(O—CO—N(C₆H₅)₂)—CCl₃ | 132 |
| 13 | — | — | —CH(O—CO—NHCH₃)—CCl₃ | 140 |
| 14 | — | — | —CH(O—CS—NH—CH₂—CH=CH₂)—CCl₃ | 147–149 |
| 15 | — | — | —CH(O—CO—N(CH₃)₂)—CCl₃ | 100–103 |
| 16 | — | — | —CH(O—CO—C₆H₄-3-NO₂)—CCl₃ | 94 |
| 17 | — | — | —CH(O—CO—C₆H₃-2,4-Cl₂)—CCl₃ | oil, identified using NMR |
| 18 | — | — | —CH(O—CO—C₆H₄-4-Cl)—CCl₃ | 135 |
| 19 | — | — | —CH(O—CO—C₆H₄-3-CF₃)—CCl₃ | 60 |
| 20 | — | — | —CH(O—CO—C₆H₄-4-CH₃)—CCl₃ | 110 |
| 21 | — | — | —CH(O—CO—C₆H₄-3-CH₃)—CCl₃ | 57 |

TABLE I-continued

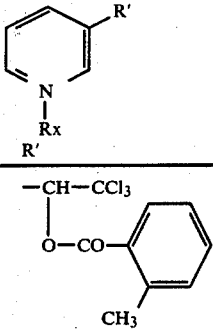

| Compound | R | X | R' | mp (°C) | |
|---|---|---|---|---|---|
| 22 | — | — | —CH—CCl₃ with O—CO—(o-tolyl) | 61 | |
| 23 | —CH₃⊕ | Cl⊖ | —CHOH—CCl₃ | 215 | |
| 24 | —C₂H₅⊕ | I⊖ | —CHOH—CCl₃ | 172 | |
| 25 | -n-C₄H₉⊕ | Br⊖ | —CHOH—CCl₃ | 197 | |
| 26 | -n-C₇H₁₅⊕ | Br⊖ | —CHOH—CCl₃ | 170 | |
| 27 | —CH₂—C₆H₅⊕ | Br⊖ | —CHOH—CCl₃ | 210 | |
| 28 | —H⊕ | I⊖ | —CHOH—CCl₃ | 196 | (Decomposition) |
| 29 | —H⊕ | 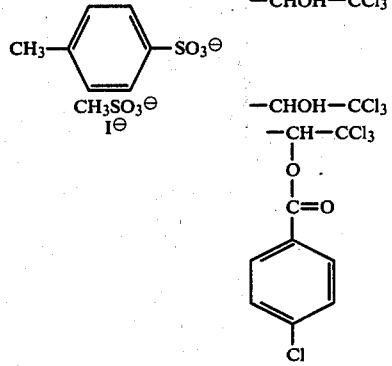 | —CHOH—CCl₃ | 163 | tion) |
| 30 | —H⊕ | CH₃SO₃⊖ | —CHOH—CCl₃ | 117 | |
| 31 | —CH₃⊕ | I⊖ | —CH—CCl₃ with O—C(=O)—(p-Cl-phenyl) | 137 | |
| 32 | —CH₃⊕ | I⊖ | 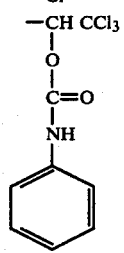 | 155 | |

The process for preparing 1-(3-pyridyl)-2,2,2-trihaloethanols, in accordance with the above defined formulas, wherein in formula 1, n is O, and in formula II, A is H, comprises reacting pyridine-3-aldehyde in the presence of strong bases with a compound HCVYZ, in which VYZ represent chlorine or bromine, and V, Y, Z may be identical or different, but are preferably identical.

Compounds of the formula HCVYZ, such as HCCl₃, HCBr₃, HCBr₂Cl and HCBrCl₂ can be used in large excess relative to the pyridine-3-aldehyde. A molar ration of the trihalomethane compound to pyridine-3-aldehyde, such as 6:1, preferably 3:1, has proved advantageous. The reaction may also be carried out with smaller amount of trihalomethane. It is advisable, however, to work with at least a molar amount corresponding to the reacton equation, i.e., a molar ratio of 1:1.

Strong bases according to the present process are alkali metal hydroxides, alkali metal amides, salts of strong bases and weak acids, as well as alkali metal alcoholates. In particular, hydroxides and amides of potassium and sodium, especially also sodium tert.-butylate and potassium tert.-butylate have proved useful, the latter compound having proved preferable for the preparation of 1-(3-pyridyl)-trihaloethanols.

Relative to the pyridine-3-aldehyde, the amount of the alkaline condensation agent used may vary within a wide range. A molar ratio of pyridine-3-aldehyde to the alkaline condensation agent of 1:0.2 to 2, preferably 1:1 to 1.5, is advantageous. Solvents for carrying out the present reaction are alcohols, for example methyl, ethyl, propyl and butyl alcohols, preferably tert.-butyl alcohol, and also ethers, for example diethyl ether, dioxan and inert solvents such as benzene, toluene and xylene.

The reaction of the pyridine-3-aldehyde with the different trihalomethanes proceeds at temeratures between −40° and +25° C., preferably between −10° and +10° C., and requires a rather long reaction time, in general lasting from 2 to 5 hours.

A suitable method of carrying out the process is to add the strong base in small quantities to the mixture of pyridine-3-aldehyde and the trihalomethane. To facilitate the dosing, the above-mentioned solvents can be used, and with their assistance the basic condensation agents can be added to the reaction mixture.

When the reaction is complete, the reaction mixture is treated with water and a pure product is obtained by customary isolation methods, for example, by extraction, using solvents such as chloroform, methylene chloride or ether and, if desired, subsequent recrystallisation.

The process for the preparation of N-oxide compounds, in which in formula I, R is oxygen, $m=0$, and $n=1$, and in formula II, A is preferably H, is carried out by reacting with organic or inorganic per-compounds, compounds of the following definitions:

a. Compounds defined by formulas I to IV wherein in formula I, n is O, and formula II A is H.

b. Compounds definec by formulas I to IV wherein in formula I, n is O, in formula II, A=formula III, with B' representing oxygen or sulphur, preferavbly oxygen, B an aliphatic radical having from 1-12 C-atoms, or an optionally substituted aromatic radical.

c. Compounds defined by formulas I to IV, wherein in formula I, $n=0$, also in formula I, R' is a radical of the general formula II, in which V, Y and Z are identical and represent Cl or Br, A represents preferably H or has the meaning given by formula III, in which B represents an optionally substituted aromatic radical, and B' may represent an oxygen atom, or A may be a sulphonyl group of the general formula —SO$_2$—B, in which B represents an aliphatic radical having from 1 to 10 C-atoms, or an optionally substituted aromatic radical.

Starting compounds for oxidation with per-compounds are the following 1-(3-pyridyl)-2,2,2-trihaloethyl compounds:

1-(3-pyridyl)-2,2,2-trichloroethanol
1-(3-pyridyl)-2,2,2-dichlorobromomethanol
1-(3-pyridyl)-2,2,2-tribromoethanol
1-(3-pyridyl)-2,2,2-dibromochloroethanol
[1-(3-pyridyl)-2,2,2-trichloroethyl] esters and also
[1-(3-pyridyl)-2,2,2-tribromoethyl] esters of aliphatic acids and aromatic acids, in which the aromatic radical may be optionally substituted. Substituents of the aromatic radical are, for example, halogen, alkyl, haloalkyl, alkoxy, acyl, nitro, ester and COOH groups.

Individual examples of these types of ester are:
1-(3-pyridyl)-2,2,2-trichloroethyl acetate
1-(3-pyridyl)-2,2,2-trichloroethyl propionate
1-(3-pyridyl)-2,2,2-trichloroethyl β-methylbutyrate
1-(3-pyridyl)-2,2,2-tribromoethyl caproate
1-(3-pyridyl)-2,2,2-tribromoethyl caprate
1-(3-pyridyl)-2,2,2-trichloroethyl benzoate
1-(3-pyridyl)-2,2,2-tribromoethyl benzoate
1-(3-pyridyl)-2,2,2-trichloroethyl monochlorobenzoate
1-(3-pyridyl)-2,2,2-tribromoethyl monochlorobenzoate
1-(3-pyridyl)-2,2,2-trichloroethyl methylbenzoate
1-(3-pyridyl)-2,2,2-trichloroethyl trifluoromethylbenzoate
1-(3-pyridyl)-2,2,2-tribromoethyl trifluoromethylbenzoate
1-(3-pyridyl)-2,2,2-trichloroethyl monobromobenzoate
1-(3-pyridyl)-2,2,2-tribromoethyl monobromobenzoate
1-(3-pyridyl)-2,2,2-trichloroethyl 2,4-dichlorobenzoate
1-(3-pyridyl)-2,2,2-trichloroethyl organosulphonate
1-(3-pyridyl)-2,2,2-tribromoethyl organosulphonate
in which the organo radical of the sulphonate represents an aliphatic, branched or straight-chain alkyl radical having from 1 to 10 carbon atoms, or an aromatic radical which may, if desired, be substituted.

Examples of substitution radicals are halogens, for example fluoro, bromo and chloro groups, and also alkyl or haloalkyl, alkoxy, acyl or nitro groups.

Individual examples of this type of compound are:
1-(3-pyridyl)-2,2,2-trichloroethyl methanesulphonate
1-(3-pyridyl)-2,2,2-trichloroethyl benzenesulphonate
1-(3-pyridyl)-2,2,2-tribromoethyl benzenesulphonate Suitable per-compounds are peroxides, such as alkali metal peroxides, peroxosulphates, and peracids, for example peracetic acid, perphthalic acid, peroxosulphuric acid, preferably H$_2$O$_2$ and chloroperbenzoic acid.

The organic per-compounds are used, relative to the pyridyl compounds, in the molar ratio of 1 to 2:1, preferably 1 to 1.5:1.

Solvents that are suitable for carrying out the process are methylene chloride, ethylene chloride, chloroform and acetic acid. When using H$_2$O$_2$, it is advisable to use water, methanol, acetic acid and acetic acid anhydride as solvents.

The temperature applied during the reaction lies between 0° and 100° C., preferably between 50° and 80° C.

The process for the preparation of compounds in which R in formula I represents a hydrogen atom or an aliphatic radical having from 1 to 12 C-atoms or an aralkyl radical having from 7 to 12 C-atoms, which may, if desired, be substituted, and wherein in formula II, preferably A=H, may be obtained by reacting the same compounds as listed under a, b and c (noted previously) with compounds of the formula RX, in which X is halogen or an SO$_3$R" radical, in which R" has the meaning OR, OH or an aryl or alkyl group.

Successful 1-(3-pyridyl)-2,2,2-trihaloethyl compounds as defined under a, b and c are all compounds and compound classes that, as described in the above text, have proved advantageous for the oxidation with per-compounds.

1-(3-pyridyl)-2,2,2-trihaloethyl compounds that are especially suitable for the process for the preparation of the compounds in which in formula I, R=H or an aliphatic radical having 1-12 C-atoms or an aralkyl radical with 7-12 C-atoms, which may be substituted, and in formula II, A=H are 1-(3-pyridyl)-2,2,2-tribromoethanol, preferably 1-(3-pyridyl)-2,2,2-trichloroethanol.

Halogen compounds of the formula RX may chiefly be bromide, chloride and iodide compounds. Suitable substituents of the aralkyl radical, especially on the aromatic portion, are chlorine radicals, although other substituents may be considered. As aliphatic radicals having from 1 to 12 C-atoms, alkenyl groups and alkyl radicals of the branched or, preferably, straight-chain type are reactant groups which may be used, these groups also being suitable for the aliphatic portion of the aralkyl radical.

Examples of the alkyl halide compounds are:
methyl chloride, methyl bromide, methyl iodide, ethyl chloride, ethyl bromide, ethyl iodide, propyl chloride, propyl bromide, propyl iodide, butyl chloride, butyl bromide, amyl bromide, hexyl bromide, heptyl bromide, isopropyl bromide, isopropyl chloride and allyl chloride.

The aralkyl radical of the formula RX may contain a six-membered hydrocarbon aromatic substance, although aromatic systems having a higher number of members, to which a further aromatic member may be fused, are also possible.

Suitable examples of the compound class of aralkyl halides are phenylalkyl halides, having from 7 to 12 C-atoms which may be chlorinated on the phenyl radical, for example, benzyl bromide, benzyl chloride, benzyl iodide, p-chlorobenzyl chloride, m-chlorobenzyl chloride, 2,4,6-trichlorophenylbutyl chloride and 2,5-dichlorophenylhexyl bromide.

Reactants of the formula type $RSO_3R''$, in which $R''$ represents OR, are, for example, sulphates, such as dimethyl sulphate, diethyl sulphate, dipropyl sulphate, dibutyl sulphate and diamyl sulphate.

Examples of the compounds of the formula $RSO_3OH$ that may be mentioned are methyl sulphuric acid, ethyl sulphuric acid and propyl sulphuric acid.

Sulphonic acid compounds of the defined formula type $RSO_3R''$ may be alkyl esters of aryl or alkyl sulphonic acids, these esters being the branched, preferably, straight-chain type and having from 1 to 12 C atoms, or phenylalkyl esters of aryl or alkyl sulphonic acids these esters having from 7 to 12 C-atoms and being optionally substituted, preferably substituted by chlorine. Sulphonic acids from the ester compounds are aromatic sulphonic acids, for example, benzenesulphonic acid, and toluenesulphonic acid and also straight and branched chain alkyl sulphonic acids having from 1 to 10 C-atoms. Halogen, nitro and alkoxy radicals may be substituents of benzene sulphonic acid.

Compounds of this type are:
methyl benzenesulphonate
isobutyl benzenesulphonate
benzyl p-toluenesulphonate
4-chlorobenzyl p-toluenesulphonate
propyl ethanesulphonate
benzyl 2-methyl-1-butanesulphonate.

1-(3-pyridyl)-2,2,2-trihaloethyl compounds and compounds of the formula type RX may be used in the molar ratio of 1:1 to 30.

The reaction temperatures are 20° C. to 200° C., preferably 60° to 160° C. and the reaction pressure is from 0 to 10 atmospheres, wherein as dissolving intermediaries there may be used, for example, dioxan, tetrahydrofuran, chloroform and dimethylformamide; if desired the latter may also be used as a catalyst.

The preparation of the compounds defined by formula I to IV, wherein in formula I, R is hydrogen, and in formula II, A=H is accomplished by reacting compounds a, b, c, as defined above with organic or inorgainc acids.

1-(3-pyridyl)-2,2,2-trichloroethyl compounds for carrying out the process are all those substances that have been described in the above text for the oxidation with per-compounds. Preferably, however, these are:
1-(3-pyridyl)-2,2,2-trichloroethanol
1-(3-pyridyl)-2,2,2-dichlorobromoethanol
1-(3-pyridyl)-2,2,2-tribromoethanol
1-(3-pyridyl)-2,2,2-dibromochloroethanol.

Suitable inorganic acids have proved to be hydrogen iodide, but especially hydrogen chloride and hydrogen bromide, and also $H_2SO_4$ and phosphoric acid, all of which may also be used as aqueous solutions.

Organic substances of the type claimed are aliphatic monocarboxylic and polycarboxylic acids, aromatic carboxylic acids, which may, if desired, be substituted, and also aliphatic sulphonic acids and aryl sulphonic acids.

Organic aliphatic carboxylic acids of the type mentioned are, in particular, those having from 2 to 10 C-atoms Examples thereof are preferably the saturated, straight-chain monocarboxylic acids having from 2 to 10 C-atoms, although branched-chain compound types, such as β-methylbutyric acid, are possible. Among the dicarboxylic acids, the straight-chain, saturated examples having from 2 to 10 C-atoms are examples of addition components for the pyridyl compounds used.

Substituents of the aromatic carboxylic acids, preferably benzoic acid, may be alkyl, especially methyl, halogen and nitro groups. Individual examples thereof are tolyl acids, mono- and dichlorobenzoic acids, mono- and dibromobenzoic acids and also nitrobenzoic acids. For the pyridyl compounds of the type c above, suitable reactants are organosulphuric acids, for example alkysulphuric acids, such as methysulphuric acid, ethylsulphuric acid, and likewise organosulphonic acids, in which the organo radical of the sulphonic acid as an aliphatic, straight-chain alkyl radical, having e.g. from 1 to 10 C-atoms, or is an aromatic radical, preferably a phenyl radical which may be substituted, if desired. Halogen and alkyl groups and nitro and alkoxy radicals may be substituents. Examples of this kind are benzenesulphonic acid, p-toluenesulphonic acid, chloronitrobenzenesulphonic acids, nitrobenzenesulphonic acids, monobromobenzenesulphonic acids, dimethylbenzenesulphonic acids, methylethylbenzenesulphonic acids, 3-bromo-4-methoxy-benzenesulphonic acids, 2-chlorotoluenesulphonic acid-(4), 2-bromotoluenesulphonic acid-(4) and methanesulphonic acid.

The molar ratio of the 1-(3-pyridyl)-2,2,2-trihaloethyl compounds to inorganic or organic acids is 1:1 to 20, the reaction temperature is from 15° to 50° C.; suitable dissolving intermediaries are dioxan and chloroform.

The preparation of the 1-(3-pyridyl)-2,2,2-trihaloethyl esters as defined by compound b. is carried out by reacting the compound a. with

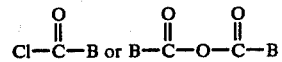

or ketene, in which B is an aliphatic radical having from 1 to 10 C-atoms, or an aromatic radical which may be optionally substituted, or an aralkyl radical having from 7 to 12 C-atoms, optionally substituted, if desired in the presence of an acid-binding agent. Suitable acid chlorides of the method used, in which B is an aliphatic radical, may be branched or straight chain, saturated monocarboxylic acid chlorides. Examples are: acetyl chloride, propionyl chloride, butyryl chloride, β-methylbutyryl chloride, valeryl chloride, oenanthyl chloride, capryl chloride, pelargonic acid chloride and capric acid chloride.

A suitable acid chloride with the mentioned aromatic radical is benzoic acid chloride which may optionally contain substituents such as alkoxy, acyl, ester, COOH groups, halogen, alkyl groups, such as methyl, ethyl, propyl, butyl and valeryl groups, haloalkyl groups, for example halomethyl, haloethyl and nitro groups. Individual substances are p-methoxybenzoic acid chloride, terephthalic acid monomethylester chloride, m-chlorobenzoic acid chloride, p-chlorobenzoic acid chloride, 2,4-dichlorobenzoic acid chloride, p-bromobenzoic acid chloride, m-bromobenzoic acid chloride, o- or p- or m-methylbenzoic acid chloride, o- or m- or p-trifluoromethylbenzoic acid chloride, p-trichloromethylbenzoic acid chloride, p-nitrobenzoic acid chloride and m-nitrobenzoic acid chloride.

The molar ratio of aliphatic or aromatic acid chlorides to the amount of the 1-(3-pyridyl)-2,2,2-trihaloethanol of compound a. amounts to 1 to 5:1.

The radical B in the used acid anhydrides is an aliphatic radical, which may be an alkyl radical having from 1 to 10 C-atoms, for example a $CH_3$-group. 1-(3-pyridyl)-2,2,2-trihaloethanol compounds and acid anhydride are used in the molar ratio of 1:1 to 10. The same molar ratio applies to the use of ketene. The addition of small amounts of alkali metal carboxylic acid salts, such as Na-acetate, is advisable in the case of ester formation which acid anhydrides. Dissolving intermediaries, which are to be used, if desired, in the esterification of the 1-(3-pyridyl)-2,2,2-trihaloethanols, are methylene chloride, chloroform or inert dissolving intermediaries, such as dioxan, benzene, toluene or xylene. This is recommended, for example, when esterification with acid chlorides is carried out, but may also contribute to good progress of the reaction in the esterification with anhydrides when the anhydride used does not itself take over the role of the dissolving intermediary.

To carry out the reaction, optionally required acid-binding agents are, for example, pyridine, and also alkali metal and alkaline earth metal carbonates, -hydrogen bicarbonates and -oxides, for example $K_2CO_3$ and $Na_2CO_3$, or tertiary amines, for example triethylamine.

The molar ratio of the 1-(3-pyridyl)-2,2,2-trihaloethanol of compound type a. to pyridine is 1:10 to 20, while in the case of the tertiary amines a molar ratio of 1:1 to 3 is expedient. The use of the acid-binding agents is advantageous when the esterification is to be carried out using the defined acid chlorides. The reaction temperatures for preparing the 1-(3-pyridyl)-2,2,2-trihaloethyl esters of the defined acids range between 0° to 160° C.

The preparation of the [1-(3-pyridyl)-2,2,2-trihaloethyl]-carbamate compounds according to formulas I to IV wherein in formula I, n=O, and in formula II A=- formula III, with B' being oxygen or sulphur, preferably oxygen, and B=formula IV, is carried out by reacting 1-(3-pyridyl)-2,2,2-trihalo-ethanols, in which in formula I, n=O, and in formula II, A=H, with

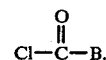

or with F–N=C=B', wherein B' is sulphur or oxygen, F and D are the same or different, and are hydrogen or aliphatic radicals having from 1 to 10 C-atoms, or aromatic radicals or aralkyl radicals having from 7 to 12 C-atoms.

Promising aliphatic radicals having from 1 to 10 C-atoms, are for example, branched and straight-chain alkenyl and alkyl groups. The aromatic radical, such as the phenyl radical, may optionally be substituted. Possible substituents are, for example, alkyl, alkenyl, nitro and alkoxy radicals, also halogen and haloalkyl radicals, wherein halogen may mean iodine, bromine, chlorine or fluorine.

Examples of such thiocarbamic acid chloride compounds are, for example, thiocarbamic acid chloride and the N-mono- or di-substituted derivatives thereof, such as N-phenylthiocarbamic acid chloride, N,N-diphenylthiocarbamic acid chloride, N,N-di-(n-butyl)-thiocarbamic acid chloride, and N,N-di-(2,4-dichlorodiphenyl)-thiocarbamic acid chloride.

Examples of the compound class of carbamic acid chlorides are, for example, carbamic acid chlorides, N,N-dimethylcarbamic acid chloride N,N-diethylcarbamic acid chloride, N-heptyl-N-ethylcarbamic acid chloride, N,N-diphenylcarbamic acid chloride, N-(3-fluorophenyl)-carbamic acid chloride, N-(3-iodophenyl)-carbamic acid chloride, N,N-di-(3-nitroisopropyl)-carbamic acid chloride, N-(o-tolyl)carbamic acid chloride, N-heptyl-N-allycarbamic acid chloride, N-(2,4,4'-tri-chlorodiphenyl)-carbamic acid chloride, N-methoxy-N-ethyl-carbamic acid chloride and N-methyl-N-(2-nitrophenyl)-carbamic acid chloride.

To carry out the reaction, 1-(3-pyridyl)-2,2,2-trihaloethanol is reacted with the carbamic acid chloride compound or the thiocarbamic acid chloride compound, advantageously in a molar ratio of 1:1 to 3. The temperatures applied range from 20° to 100° C., preferably from 40° to 80° C.

In general, acid-binding agents are required to form carbamates. Basically, the same steps have to be taken with regard to the choice of the suitable acid acceptors and the number of moles used as those taken with the corresponding 1-(3-pyridyl)-2,2,2-trihaloethanol compound in the esterification of 1-(3-pyridyl)-2,2,2-trihaloethanols with the above-mentioned compounds according to the formula

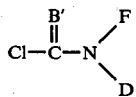

Solvents may be used, if desired, in this reaction too, dioxan, methylene chloride, ethylene chloride, chloroforml or inert solvents, such as benzene, xylene and toluene, being suitable.

The isocyanates claimed, for example phenylisocyanate, o- or p-trifluoromethylphenylisocyanate, o- or m- or p-fluorophenylisocyanate, 3,4-dichlorophenylisocyanate, methylisocyanate, ethylisocyanate, propylisocyanate, and α-methylpropylisocyanate, and isothiocyanates, for example, methylisothiocyanate, ethylisothiocyanate, allylisothio-cyancyanate, p-toluylisothiocyanate, p-ethoxyphenylisothiocyanate, phenylisothiocyanate, p-chlorophenylisothiocyanate, 3,4-dichlorophenylisothiocyanate and p-nitrophenylisothiocyanate are used, relative to the corresponding 1-(3-pyridyl)-trihaloethanol compound, in the molar ratio of 1 to 20:1, operation being carried out at temperatures ranging between 20° and 80° C., if desired, under autogenous pressure. Solvents suitable for this particular reaction are polar solvents, such as dioxan, tetrahydrofuran and chloroform.

A good reaction result may be produced by additional catalysts, such as dibutyltin laurate or triethylamine.

The preparation of the organosulphonic acid 1-(3-pyridyl)-2,2,2-trihaloethyl esters according to formulas I to IV is accomplished by reacting 1-(3-pyridyl)-2,2,2-trihaloethanols, wherein in formula I, n=O and in formula II A=H, if appropriate in the presence of acid-binding agents, with $Cl—SO_2B$, wherein B represents an aliphatic radical having from 1 to 10 C-atoms, or an aromatic radical, optionally substituted.

The aromatic radical is, in particular, a phenyl radical which may optionally contain substituents such as alkyl, nitro, hydroxyl, carboxy, alkoxy and halogen radicals, as well as haloalkyl radicals, wherein halogen may mean iodine, bromine, chlorine or fluorine.

Examples of this type of aromatic sulphochlorides are for example, benzene sulphochloride, p-toluene sulphochloride, 4-octylbenzenesulphochloride, 1-hydroxy-2- carboxybenzene-4-sulphochloride, 3-nitrobenzene sulphochloride, 1-methoxy-benzene-4-sulphochloride, 2-nitro-toluene-4-sulphochloride, 4-chlorobenzene sulphochloride, 4-bromobenzene sulphochloride, 4-iodobenzene sulphochloride, 4-fluorobenzene sulphochloride, 2,5-dichlorobenzene-4-sulphochloride, 1-chloro-2-nitro-benzene-4-sulphochloride.

Successful examples of the class of compounds Cl—$SO_2B$ may be compounds in which B is a branched or straight chain alkenyl or alkyl group which may optionally be substituted.

A few examples of this type of compound are: methanesulphonylchloride, ethanesulphonylchloride, propane-1-sulphonylchloride, isopropane-1-sulphonylchloride, butane-1- sulphonylchloride, isobutane-1-sulphonylchloride, 2-methylbutane-1-sulphonylchloride, pentane-1-sulphonylchloride, hexane-1-sulphonyl-chloride, heptane-1-sulphonylchloride, 3-allylbutane-1-sulphonylchloride, octane-1-sulphonylchloride, oct-6-ene-1-sulphonylchloride, nonane-1-sulphonylchloride, 2,4,6-trimethylhexane1-sulphonylchloride, 2,4-diethyl-butane-1-sulphonylchloride, 4-methylpentane-2-sulphonylchloride.

The molar ratio of compounds of the Cl—$SO_2B$ type to the amount of 1-(3-pyridyl)-trihaloethanol used is 1 to 5:1, and the reaction temperatures range between 0° and 160° C.

Solvents that are suitable for the preparation of the sulphonic acid esters are methylene chloride, ethylene chloride, chloroform, dioxan and tetrahydrofurane, or inert solvents, such as benzene, toluene or xylene. The acid-binding agents to be used if desired may be, for example, pyridine, alkali metal and alkaline earth metal carbonates and oxides, for example $K_2CO_3$, $Na_2CO_3$, and MgO, or tertiary amines, for example, triethylamine. The molar ratio of 1-(3-pyridyl)-2,2,2-trihaloethanol to pyridene is 1:10 to 20, while in the case of the tertiary amines a molar ratio of 1:1 to 3 is advantageous.

The invention further relates to fungicidal agents, characterized by a content of one or more of the above described compounds. Preferred are fungicide agents containing one or more compounds of the general formulas I to IV, wherein 1. in formula I n is O and in formula II A is H;
2. in formula I R is oxygen, m is O, n is 1 and preferably in formula II A is H;
3. in formula I R is H or an aliphatic radical having from 1 to 12 C-atoms or an aralkyl radical with 7 to 12 C-atoms, optionally substituted, and preferably in formula II A is H;
4. in formula I n is O, and in formula II A has the meaning given in formula III in which B' is oxygen or sulphur, preferably oxygen, and B is an aliphatic radical having from 1 to 10 C-atoms or an aromatic, optionally substituted, radical;
5. in formula I n is O, and in formula II A is represented by formula III in which B' is oxygen or sulphur, preferably oxygen and B is represented by formula IV, wherein F and D are defined as above;
6. in formula I n is O, R' is a radical of the general formula II, in which V, Y and Z are identical and represent Cl or Br, A is preferably H or has the meaning given by formula III in which B is an aromatic radical, if desired substituted, and B' is oxygen, A also representing a sulphonyl group of the general formula —$SO_2$—B, in which B represents an aliphatic radical having from 1 to 10 C-atoms, or an aromatic radical;
7. distinctive marks are the same as in 6. except that n is 1 instead of O and R is oxygen or hydrogen, and when R is hydrogen, X represents a negative ion and m is ½ or 1, and when R is oxygen m is 0.

1-(3-pyridyl)-1-hydrogen-2,2,2-trichloroethane is especially distinguished among the great number of compounds mentioned on account of its quite special fungicidal action, also the N-oxide thereof and the corresponding ethanes substituted by bromine instead of chlorine. Further highly effective compounds may be learned from the examples.

The action of the inventive fungicides is preferably directed against various types of mildew, for example, cucumber mildew, barley mildew, rose mildew, apple mildew, etc.; the agents also have an especially good action against harmful fungi originating in the soil.

The fungicides have a systemic action and are also contact fungicides. It sometimes happens that one agent acts more effectively systemically, and another is more active as a contact fungicide. For example, the compound in which the OH-group of the fundamental compound 1-(3-pyridyl)-1-hydroxy-2,2,2-trichloroethane is esterified with a benzoyl radical is especially effective as a contact fungicide.

The compounds according to the invention may be applied as they are, but in general they are used as mixtures, with a content of active substance of at least 0.01 to a maximum of 95% by weight. The preferred forms of application are spray powders and emulsion concentrates, but granules and microcapsules can also be used,. They are generally applied by pouring or spraying.

The spray powders usually contain 10 to 80% by weight, preferably from 40 to 80% by weight of one or more active substances, wetting agents in quantities of from about 1 to 10% by weight, for example lignin sulphonates, alkyl and alkylaryl sulphonates, or polyethers. Fillers are furthermore frequently added in quantities of from 10 to 89% by weight. Examples of fillers are talcum, bentonite and China clay.

The emulsion concentrates are prepared in quantities with frequently 10 to 60% by weight, preferably 15 ot 40% by weight of one or more active substances. They contain dispersing auxiliaries or emulsifiers in quantities of from 1 to 10% by weight. Examples of emulsifiers are neutral, anionic or cationic substances, such as alkylaminocarboxylic acids, aryl and alkylaryl sulphonates; dispersants are polyethers, etc. Solvents are used in amounts of from 30 to 89% by weight. Examples of solvents are aliphatic alcohols, for example butanol, xylene, dimethylformamide, dimethylsulphoxide and N-methylpyrrolidone. It is often an advantage to use mixtures of solvents, especially mixtures of non-polar or only slightly polar solvents wth strongly polar solvents. In this case, about 10 to 50% by weight, corresponding to the total proportion of solvent, of strongly polar solvents are required.

The invention further relates to dressing agents for seed, which contain as active ingredient one or more of the above described compounds. Preferred are seed dressing agents containing one or more compounds of the general formulas I to IV, wherein 1. in formula I n is O and in formula II A is H;
2. in formula I R is oxygen, m is O, n is 1 and preferably in formula II A is H;
3. in formula I R is H or an aliphatic radical having from 1 to 12 C-atoms or an aralkyl radical with 7 to 12 C-atoms, optionally substituted, and preferably in formula II A is H;

4. in formula I n is O, and in formula II A has the meaning given in formula III, in which B' is oxygen or sulphur, preferably oxygen, and B is an aliphatic radical having 1 to 10 C-atoms or an aromatic, optionally substituted, radical;

5. in formula I n is O, and in formula II A is represented by formula III, in which B' is oxygen or sulphur, preferably oxygen, and B is represented by formula IV, wherein F and D are defined as above;

6. in formula I n is O, R' is a radical of the general formula II, in which V, Y and Z are identical and represent Cl or Br, A is preferably H or has the meaning given by formula III in which B is an aromatic radical, if desired substituted, and B' is oxygen, A also representing a sulphonyl group of the general formula —SO₂—B, in which B represents an aliphatic radical having from 1 to 10 C-atoms, or an aromatic radical;

7. distinctive marks are the same as in 6. except that n is 1 instead of O and R is oxygen or hydrogen, and when R is hydrogen, X represents a negative ion and m is ½ or 1, and when R is oxygen m is O.

When used as dressing agents for seed, the compounds are applied to the seed, plant tubers or plant bulbs directly. The compounds may also be used with additives, for example for an improved adherence of the active substance.

The compounds of the invention may be used both in d- or l-form, and also as racemates.

Other objects and features of the present invention will become apparent from the following detailed examples. It is to be understood that the examples are designed for purposes of illustration only, and are not intended as a definition of the limits and scope of the invention disclosed.

EXAMPLE 1

Preparation of the compound:

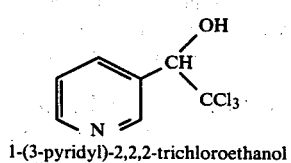

1-(3-pyridyl)-2,2,2-trichloroethanol

A solution of 59 grams of potassium tert.-butylate in 400 ml of tert.-butanol was added to a solution, cooled to 0° C., of 32 grams of freshly distilled pyridine-3-aldehyde in 149 grams of chloroform within a period of 2 hours; during doing this the reaction mixture was stirred and cooled in such a manner that it did at no time become any warmer than 6° C. Stirring was then continued for 1 hour at 0° C., 150 ml of absolute benzene were added, and stirring was continued for another 2.5 hours at 0° C. Subsequently the brown reaction mixture was slowly poured into ice-cooled dilute H₂SO₄ (prepared from 13.7 ml of concentrated H₂SO₄ and a mixture of ice and water), and the mixture was extracted several times with chloroform. The combined chloroform solutions were washed with water, dried over Na₂SO₄ and concentrated by evaporation. The remaining crystalline crude product was recrystallised from aqueous methanol (70 ml of methanol + 110 ml of water), and 36.0 grams of yellowish-white crystals were thereby obtained having a melting point of 141° C.

Analysis values: $C_7H_6Cl_3NO$. Calculated % by weight C. 37.12; H. 2.67; N, 56.18. Found % by weight C. 36.85; H. 2.62; N, 6.16.

EXAMPLE 2

Preparation of the compound:

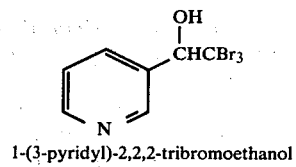

1-(3-pyridyl)-2,2,2-tribromoethanol

A solution of 23.6 grams of potassium tert.-butylate in 160 ml of tert.-butanol was added dropwise to 12.8 grams of pyridine-3-aldehyde dissolved in 150 grams of bromoform, at 0° to 5° C. After addition was complete, stirring was carried out for 1 hour and, after the addition of 60 ml of absolute benzene, stirring was continued for another 2 hours at the same temperature. Thereafter, the reaction mixture was poured into the same amount of water and extracted by shaking three times with, in each case, 100 ml of CH₂Cl₂. The combined organic extracts were dried over Na₂SO₄/active charcoal, and concentrated by evaporation. The remaining dark oil was brought to crystallization by rubbing with methanol. After recrystallizing twice from methanol/active charcoal, 12.8 grams of light brown crystals were obtained having a melting point of 163° C.

Analysis values: $C_7H_6Br_3NO$. Calculated % by weight C, 23,36; H, 1.68; N, 3.89. Found % by weight C, 23,57; H, 1.74; N, 3.92.

EXAMPLE 3

Preparation of the compound:

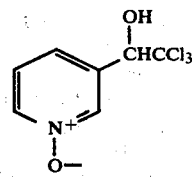

1-(3-pyridyl)-2,2,2-trichloroethanol-N-oxide 11.3 grams of 1-(3-pyridyl)-2,2,2-trichloroethanol were dissolved in 150 ml of absolute CHCl₃ and at 0° to 3° C. 15 grams of m-chloroperbenzoic acid were added in small amounts. After the addition was complete, stirring was continued for another 2 hours at room temperature. The reaction mixture was considerably concentrated and about 300 ml of ether were added thereto, the product precipitating as a colorless powder. The yield was 10.5 grams. The product was recrystallized once from THF for analysis.

Melting point 171° C.

Analysis values: $C_7H_6Cl_3NO_2$. Calculated % by weight C, 34.67; H, 2.49; N, 5.78. Found % by weight C, 34.83; H, 2.46; N, 5.78.

EXAMPLE 4

Preparation of the compound:

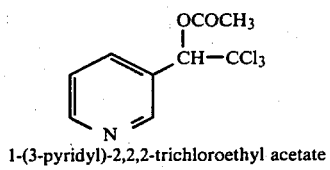

1-(3-pyridyl)-2,2,2-trichloroethyl acetate 10.0 grams of 1-(3-pyridyl)-2,2,2-trichloroethanol were dissolved in 50 ml of acetic anhydride and after the addition of 2 grams of sodium acetate, heated for 10 minutes at 90° C. and thereafter allowed to stand at room temperature for 12 hours. The reaction mixture was concentrated by evaporation in vacuo, the residue was divided between methylene chloride and aqueous saturated NaHCO$_3$ solution, and thereafter the organic phase was dried and subsequently concentrated by evaporation. The yield was 10.0 grams. After recrystallization from petroleum ether, colorless crystals were obtained having a melting point of 87° C.

Analysis values: C$_9$H$_8$Cl$_3$NO$_2$. Calculated % by weight C, 40.26; H, 3.00; N, 5.22. Found % by weight C, 40.43; H, 2.96; N, 5.28.

EXAMPLE 5

Preparation of the compound:

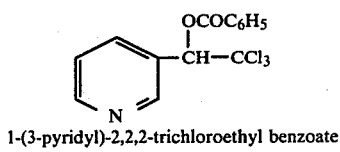

1-(3-pyridyl)-2,2,2-trichloroethyl benzoate 10 grams of 1-(3-pyridyl)-2,2,2-trichloroethanol were dissolved in 80 ml of anhydrous pyridine and 5.6 ml of benzoyl chloride were added dropwise within a period of one hour, with external cooling using ice.

Afterwards the precipitated pyridine hydrochloride was filtered off from the solution, and the filtrate was poured into a large amount of water.

After extraction of the water with chloroform, drying of the organic phase with Na$_2$SO$_4$ and distillation of the solvent from the organic portion, 7.7 grams of the 1-(3-pyridyl)-2,2,2-trichloroethyl benzoate melting at 65° C. were obtained, after recrystallization from n-hexane.

In an analogous manner, the compound 1-(3-pyridyl)-2,2,2-trichloroethyl propionate was prepared, by adding the corresponding quantity of propionic acid chloride instead of the benzoyl chloride. The melting point of the 1-(3-pyridyl)-2,2,2-trichloroethyl propionate was 35° C.

EXAMPLE 6

Preparation of the compound:

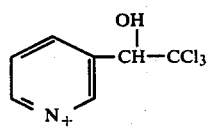

n-C$_7$H$_{15}$ Br$^-$

1-[3-(N-(n-heptyl-1)pyridinium)bromide]-2,2,2-trichloroethanol 12.0 grams of 1-(3-pyridyl)-2,2,2-trichloroethanol were dissolved in 60 ml of dioxan, 34.0 grams of n-1-heptylbromide were added thereto, and the whole was heated under reflux with 5 hours. The precipitate obtained after cooling and filtering consisted of the pure compound melting at 170° C.

In an analogous manner the compound 1-[3-(N-methylpyridinium)iodide]-2,2,2-trichloroethanol was prepared by using the appropriate quantities of methyl iodide instead of n-1-heptylbromide. The melting point of this compound was 193° C.

EXAMPLE 7

Preparation of the compound:

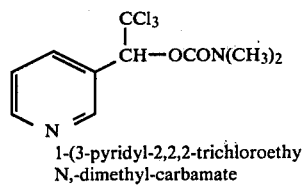

1-(3-pyridyl-2,2,2-trichloroethyl N,-dimethyl-carbamate

A solution of 10.0 grams of 1-(3-pyridyl)-2,2,2-trichloroethanol in 120 ml of absolute dioxan was heated under reflux after the addition of 7.2 grams of dimethylcarbamoyl chloride and 9 grams of K$_2$CO$_3$. The progress of the reaction was monitored by thin layer chromatography, and terminated after 200 hours with a conversion of about 50%. The reaction mixture was then filtered, the filtrate was evaporated to dryness and the dark-brown, viscous oil remaining was extracted by boiling several times with petroleum ether. From the residue remaining after evaporation of the combined extracts, 3.2 grams of colorless crystals having a melting point of 100° to 103° C. were obtained after recrystallizing several times from methanol.

Analysis value: C$_{10}$H$_{11}$Cl$_3$N$_2$O$_2$. Calculated % by weight: C, 40.36; H, 3.73; N, 9.41. Found % by weight: C, 40.71; H, 3.79; N, 9.35.

In an analogous manner the 1-(3-pyridyl)-2,2,2-trichloroethyl N,N-diethylcarbamate was obtained, by using the corresponding quantity of diethylcarbamoyl chloride instead of dimethylcarbamoyl chloride. The melting point of this compound was 62° C.

EXAMPLE 8

Preparation of the compound:

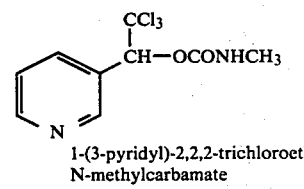

1-(3-pyridyl)-2,2,2-trichloroethyl N-methylcarbamate 10 grams of 1-(3-pyridyl)-2,2,2-trichloroethanol were dissolved in absolute dioxan and after the addition of 3.8 grams of methylisocyanate and 2 ml of triethylamine, were heated for 30 hours at 55° in a gas-tight, sealed flask. When cooled, colorless crystals precipitated, were filtered off with suction and dried. The yield was 10.9 grams. The melting point of the crystals was 140° C.

Analysis values: C$_9$H$_9$Cl$_3$N$_2$O$_2$. Calculated % by weight: C, 38.12; H, 3.20; N, 9.88. Found % by weight: C, 38.41; H, 3.33; N, 9.80.

In an analogous manner to the above embodiment, 1-(3-pyridyl)-2,2,2-trichloroethyl N-phenylcarbamate was obtained by using the appropriate quantities of phenylisocyanate instead of methylisocyanate, and heating without pressure. The product had a melting point of 146° C.

EXAMPLE 9

Preparation of the compound:

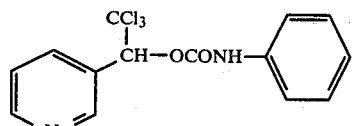

1-(3-pyridyl)-2,2,2-trichloroethyl N-phenylcarbamate 10.0 grams of 1-(3-pyridyl)-2,2,2-trichloroethanol were dissolved in 150 ml of dioxan and after the addition of 5.3 grams of phenylisocyanate, were stirred at room temperature overnight. Thereafter, the solution was divided between water and $CH_2Cl_2$, the organic phase was subsequently dried over $Na_2SO_4$ and concentrated to 10.0 grams of crude product. This was crystallized by fractionation from chloroform.

1st fraction: diphenyl urea
2nd fraction: 5.3 grams of colorless crystals melting at 146° C.

Analysis values: $C_{14}H_{11}Cl_3N_2O_2$. Calculated % by weight: C, 48.65; H, 3.21; N, 8.11. Found % by weight: C, 49.21; H, 3.25; N, 8.27.

EXAMPLE 10

Preparation of the compound:

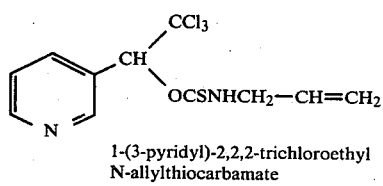

1-(3-pyridyl)-2,2,2-trichloroethyl N-allylthiocarbamate 6.0 grams of 1-(3-pyridyl)-2,2,2-trichloroethanol were dissolved in 62.1 grams of allyl isothiocyanate. 5 ml of triethylamine were added to this solution and the whole was stirred for 50 hours at room temperature. The product crystallizing out was filtered off with suction from the solution and washed with ether to give colorless crystals. Together with the product, which was isolated from the mother liquor additionally by distilling off excess allyl isothiocyanate and by subsequent recrystallization from chloroform, the total yield of the crystals obtained, which had a melting point of 147° to 148° C., was 7.0 grams.

Analysis values: $C_{11}H_{11}Cl_3N_2OS$. Calculated % by weight: C, 40.57; H, 3.41; N, 8.60. Found % by weight: C, 40.72; H, 3.34; N, 8.53.

EXAMPLE 11

Preparation of the compound:

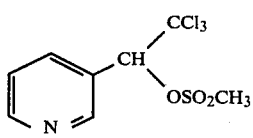

1-(3-pyridyl)-2,2,2-trichloroethyl methylsulphonate 25.0 grams of 1-(3-pyridyl)-2,2,2-trichloroethanol were dissolved in 140 ml of absolute pyridine and 19.0 grams of mesyl chloride were added dropwise over a perid of 90 minutes while cooling by ice and stirring. When the addition had been completed, the solution was stirred for 3 hours at room temperature. The reaction solution was taken up in $CH_2CL_2$, shaken out three times with aqueous saturated sodium bicarbonate solution, and 34 grams of product were isolated from the organic portion of the solution after the solvent had been evaporated. After recrystallization from chloroform, 30.8 grams of colorless crystals melting at 113° C. were obtained.

Analysis values: $C_8H_8Cl_3NO_3S$. Calculated % by weight: C, 31.55; H, 2.65; N, 4.60. Found % by weight: C, 31.51; H, 2.57; N, 4.64.

EXAMPLE 12

Greenhouse spray test to combat Barley mildew
(*Erysiphe graminis*)

Compounds 1, 2, 3, 5 and 6

In square plastic pots of 6.5×6.5 cm upper diameter, and likewise 6.5 cm high, barley plants, grown at a density of 20 to 25 plants per pot, after reaching a height of 6 to 8 cm are sprayed until dripping wet with aqueous spray liquors of the concentrations listed in Table 2. The spray liquors are prepared by stirring a 20% strength spray powder into water.

When the spray coating is dry, the test plants are placed between badly infected plants which are kept in a greenhouse at temperatures between 22° and 24° C. and at a relative atmospheric humidity of about 70%. With the assistance of a current of air produced by ventilators, conidia of *Erysiphe graminis* are transferred to the treated plants.

Evaluation was carried out after an incubation period of from 10 to 12 days. The effectiveness is given relative to the untreated control plants in accordance with the following formula:

$$100 - \frac{\text{infected leaf area treated}}{\text{infected leaf area untreated}} \times 100$$

The values determined by this method are given in Table 2 under "barley mildew contact."

Example 13

Greenhouse soaking test to combat Barley mildew
(*Erysiphe graminis*)

Compounds 1, 2, 3, 5 and 6

Barley plants, grown as described in Example 12, are soaked with 50 ml per pot of liquor of the concentrations listed in Table 2.

Further treatment and evaluation of the experiments is carried out as specified in Example 12.

The values obtained are listed in Table 2 under "Barley mildew systemic."

Example 14

Greenhouse spray test to combat cucumber mildew
(*Erysiphe cichoracearum*)

Compounds 1, 2, 3, 5 and 6

Cucumber plants, grown in plastic pots as described in Example 12, are sprayed at the two-leaf stage, after removal of the cotyledons located below the foliage leaves, with the spray liquors described in Example 12 until the plants are dripping wet.

When the spray coating has dried, the plants are contaminated with conidia of the *Erysiphe cichoracearum* fungus by uniformly dusting the surface of the leaves. The plants are subsequently kept in the greenhouse at 22° to 24° C. and a relative atmospheric humidity of about 70%.

The evaluation is carried out 15 days after contamination. The degree of infection is given as a percentage of infected leaf area relative to the control plants.

The values ascertained are listed in Table 3 under "Cucumber mildew systemic."

Example 15

Greenhouse soaking test to combat Cucumber mildew (*Erysiphe cichoracearum*)

Compounds 1, 2, 3, 5 and 6.

Cucumber plants grown as described in Example 14 are soaked with 50 ml per pot of soaking liquors prepared according to Example 13.

Further treatment and evaluation is carried out as in Example 14.

The values ascertained are listed in Table 3 under "Cucumber mildew systemic."

Example 16

Greenhouse spray test to combat Cucumber and Barley mildew

Compounds 4 and 9.

Analogously to Examples 12 and 14, cucumber and barley plants are grown and sprayed and infected as described. The results may be learned from Table 4.

Example 17

Spray test against Rose mildew in the open air

Four plants each of the roses Super Star, Roter Stern and Alain are sprayed until dripping wet with a spray liquor, prepared as described in Example 12 with 1,000 ppm content of active substance, after the natural infection had become visible. Spraying was effected four times at intervals of one week. One week after the last treatment the effectiveness, given in Table 5, is evaluated compared to four untreated control plants.

Example 18

Greenhouse spray test against Apple mildew

After the appearance of the natural infection, 4 apple seedlings on the parent stock of Malus IV (variety) in clay pots 13 cm in diameter and about 40 cm high, are sprayed until dripping wet with a spray liquor that is prepared as described in Example 12 with a content of active substance of 2,000 ppm. The spraying is effected twice with an interval of one week between treatments. One week after the last treatment, the effectiveness, given in Table 5, is evaluated in comparison to 4 untreated control plants.

Example 19

Soaking test against Apple mildew

Apple seedlings as described in Example 18 are soaked with 100 ml of soaking liquor, having an active substance content of 1,000 ppm, twice with an interval of one week between treatments. Two weeks after the last treatment, the effectiveness, given in Table 5, is evaluated in comparison to 4 untreated control plants.

Example 20

Spray test against Vine mildew (Oidium)

4 vine cuttings of the Müller-Thurgau variety in pots of 18 cm upper diameter are sprayed until dripping wet twice, at an interval of one week between sprayings, with a spray liquor prepared as described in Example 12, having a content of 2,000 ppm of active substance.

One week after the last treatment, the effectiveness given in Table 5 is evaluated in comparison to 4 untreated control plants.

Example 21

100 grams of barley seed are intimately mixed in a mixing drum with 400 milligrams of a pulverulent dressing agent formulation consisting of 50% of compound 1 and 50% of talcum. Subsequently, the seeds are sowed in pots as described in Example 12 and treatment is continued but the spraying of the active substance is omitted. The infection and evaluation is carried out likewise as described in Example 12. There is a 100% effect against established mildew as compared to the untreated comparison plants.

Example 22

50 μl of a solution or suspension of the active substance, having a content of 1,000 ppm of the active substance, are introduced together with 50 μl of a suspension of spores, produced by washing the spores from an agar culture with a nutrient solution containing 10 grams of sugar, 1 gram of glycol, 1 gram of $KH_2PO_4$ and 0.5 gram of $MgSO_4$ per liter of water, into the concave grinding of concave slides.

The slides are kept at 20° C. for 48 hours in a Petri dish, the base of which is covered with a moistened filter paper.

The ratio of the spores that have germinated to the spores that have not germinated are compared with an untreated control.

The effectiveness is calculated as a percentage according to the following formula:

$$100 \left(1 - \frac{\text{number of treated hyphae that have germinated}}{\text{number of untreated hyphae that have germinated}}\right)$$

The types of spores examined and the action of the compounds 1, 4 and 7 are given in Table 6.

The aromatic and aralkyl radicals mentioned in the claims may be optionally substituted.

Table 2

| | BARLEY MILDEW | | | | | | | | | |
|---|---|---|---|---|---|---|---|---|---|---|
| | Systemic | | | | | Contact | | | | Compound |
| ppm | 1 | 2 | 3 | 5 | 6 | 7 | 2 | 3 | 5 | 5 | number |
| 1000 | 100 | 100 | 100 | 100 | 100 | 100 | 100 | 95 | 100 | 100 |
| 500 | 100 | 100 | 100 | 100 | 100 | 100 | 100 | 90 | 100 | 100 |
| 250 | 100 | 100 | 100 | 100 | 90 | 100 | 50 | 80 | 80 | 100 |
| 125 | 100 | 100 | 100 | 90 | 70 | 90 | 90 | 80 | 60 | 90 |
| 60 | 100 | 100 | 90 | 80 | 60 | 80 | 80 | 70 | 70 | 70 |

Table 2-continued
BARLEY MILDEW

| ppm | Systemic 1 | 2 | 3 | 5 | 6 | Contact 7 | 2 | 3 | 5 | 5 | Compound number |
|---|---|---|---|---|---|---|---|---|---|---|---|
| 30 | 100 | 100 | 90 | 70 | — | 80 | 80 | 60 | 70 | — | |
| 15 | 90 | 100 | 70 | 50 | — | — | — | — | — | — | |

Table 3
CUCUMBER MILDEW

| ppm | Systemic 1 | 2 | 3 | 5 | 6 | Contact 1 | 2 | 3 | 5 | 6 | Compound number |
|---|---|---|---|---|---|---|---|---|---|---|---|
| 1000 | 100 | 100 | 100 | 100 | 100 | 100 | 100 | 95 | 100 | 100 | |
| 500 | 100 | 100 | 100 | 90 | 100 | 100 | 100 | 90 | 90 | 100 | |
| 250 | 100 | 100 | 100 | 100 | 90 | 80 | 70 | 60 | 90 | 100 | |
| 125 | 100 | 100 | 100 | 90 | 70 | 70 | 70 | 60 | 80 | 90 | |
| 60 | 100 | 100 | 90 | 90 | 60 | 60 | 60 | 50 | 80 | 70 | |
| 30 | 100 | 90 | 90 | 80 | — | 60 | 60 | — | 70 | — | |
| 15 | 90 | 90 | 75 | 70 | — | — | — | — | 50 | — | |

Table 4
CONTACT FUNGICIDE TEST

| ppm | Barley mildew 4 | 9 | Cucumber mildew 4 | 9 | Compound number |
|---|---|---|---|---|---|
| 1000 | 100 | 100 | 100 | 100 | |
| 500 | 100 | 100 | 100 | 100 | |
| 250 | 100 | 90 | 100 | 90 | |
| 125 | 100 | 80 | 90 | 90 | |
| 60 | 90 | 70 | 90 | 70 | |
| 30 | 90 | 40 | 90 | 60 | |
| 15 | 70 | — | 80 | — | |

Table 5

| Compound number | Use against | Concentration of active substance (ppm) | Effectiveness % |
|---|---|---|---|
| 1 | Rose mildew contact | 1000 | 95 |
| 1 | Apple mildew contact | 2000 | 100 |
| 1 | Apple mildew systemic | 1000 | 100 |
| 1 | Vine/Oidium contact | 2000 | 100 |

Table 6

| | Inhibition of spore germination at 1,000 ppm | | | | | | |
|---|---|---|---|---|---|---|---|
| Compound number | Alternaria | Botrytis | Fus.culm. | Fus.niv. | Phoma msd. | Seporia nod. | Vert.dahl. |
| 4 | 0 | 20 | 0 | 100 | 10 | 0 | 0 |
| 7 | 100 | 100 | 100 | 100 | 70 | 100 | 100 |
| 1 | 60 | 80 | 50 | 100 | 10 | 60 | 70 |

What is claimed is:

1. A 1-(3-pyridyl)-2,2,2-trihaloethyl compound of the general empirical formula I

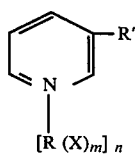

in which n is 0 or 1, R represents a member of the group consisting of oxygen, hydrogen, an aliphatic radical having from 1 to 12 C-atoms of the group consisting of alkenyl radicals and alkyl radicals of the branched or straight chain type, and an aralkyl radical having from 7 to 12 C-atoms, wherein m is 0 when R is an oxygen atom, and m is ½ or 1 when R is a hydrogen atom or an aliphatic or aralkyl radical, and X represents a negative ion of the group consisting of halogen and $SO_3R''$ radicals wherein R" has the meaning of OR, OH, an aryl or an alkyl group, and when R is H, X is a negative ion of an organic or inorganic acid; the radical R' represents a radical of the general formula II

wherein V, Y and Z each represent a chlorine or bromine atom.

2. The compound according to claim 1, wherein in formula I, n is 0.

3. The compound according to claim 1, wherein in formula I, R represents oxygen, m is 0 and n is 1.

4. The compound according to claim 1, wherein in formula I, R is a memeber of the group consisting of hydrogen, an aliphatic radical having from 1-12 C-atoms, and an aralkyl radical having from 7 to 12 C-atoms.

5. The compound according to claim 1, wherein in formula I, n is 0, R' is a radical of the general formula II, in which V, Y and Z are identical and represent Cl or Br.

6. The compound 1-(3-pyridyl)-2,2,2-trichloroethanol.

7. The compound 1-(3-pyridyl)-2,2,2-tribromoethanol.

8. The compound 1-(3-pyridyl)-2,2,2-trichloroethanol-N-oxide.

9. The compound 1-[3-(N-(n-heptyl-1)-pyridinium)-bromide]-2,2,2-trichloroethanol.

10. The compound 1-[3-(N-methyl-pyridinium)iodide]-2,2,2-trichloroethanol.

11. A fungicidal composition containing as active agent 0.01 to 95% by weight of an 1-(3-pyridyl)-2,2,2-trihaloethyl compound of the general formula I

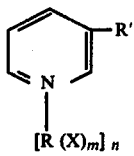

in which n is 0 or 1, R represents a member of the group consisting of oxygen, hydrogen, an aliphatic radical having from 1-12 C-atoms of the group consisting of alkenyl radicals and alkyl radicals of the branched or straight-chain type, and an aralkyl radical having from 7 to 12 C-atoms, wherein m is 0 when R is an oxygen atom, and m is ½ or 1 when R is a hydrogen atom, or an alipphatic or aralkyl radical, and X represents a negative ion of the group consisting of halogen and $SO_3R''$ radicals wherein R'' has the meaning of OR, OH, and aryl or an alkyl group, and when R is H, X is a negative ion of an organic or inorganic acid; the radical R' represents a radical of formula II

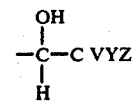

wherein V, Y, and Z each represent a chlorine or bromine atom.

12. The fungicidal composition containing as active agent 0.01 to 95% by weight of the compound according to claim 11 wherein in formula I, n is 0.

13. The fungicidal composition containing as active agent 0.01 to 95% by weight of the compound according to claim 11 wherein in formula I, R represents an oxygen atom, m is 0 and n is 1.

14. The fungicidal composition containing as active agent 0.01 to 95% by weight of the compound according to claim 11 wherein in formula I, R is a member of the group consisting of hydrogen, an aliphatic radical having from 1-2 C-atoms, and an aralkyl radical having from 7-12 C-atoms.

15. The compound according to claim 1, wherein in formula I, n is 1 and R is oxygen or hydrogen, in which, when R is hydrogen, X is a negative ion, and m is ½ or 1, and in which, when R is oxygen, m is 0, and R' is a radical of the general formula II, in which V, Y and Z are identical and represent Cl or Br.

* * * * *

UNITED STATES PATENT AND TRADEMARK OFFICE
CERTIFICATE OF CORRECTION

PATENT NO. : 4,189,486
DATED : FEBRUARY 19, 1980
INVENTOR(S) : SAUTER ET AL.

It is certified that error appears in the above—identified patent and that said Letters Patent is hereby corrected as shown below:

Column 2, line 36, change "sulphonyll" to --sulphonyl--.
Column 7, line 16, change "preferavbly" to --preferably--.
Column 9, line 65, after "atoms", insert --.--. Column 10, line 13, change "as" to --is--. Column 12, lines 30-31, change "chloroforml" to --chloroform--. Column 16, line 2, change "N, 56.18" to --N 6.18--. Column 18, line 21, change "10.0 grams" to --10.9 grams--. Column 20, line 2, change "perid" to --period--. Column 21, line 11, change "mildew systematic" to --mildew contact--. Column 22, Table 2, change the first line to read --ppm 1 2 3 5 6 1 2 3 5 6 Compound Number--; change the last two columns to read:
--6      Compound number
  100
  100
  100
   90
   70
   --
   -- --.
Column 23, Table 3, change the last two columns to read:
--6      Compound number
  100
  100
  100
   90
   70
   --
   -- --.

UNITED STATES PATENT AND TRADEMARK OFFICE
CERTIFICATE OF CORRECTION

PATENT NO. : 4,189,486
DATED : FEBRUARY 19, 1980
INVENTOR(S) : SAUTER ET AL.

It is certified that error appears in the above—identified patent and that said Letters Patent is hereby corrected as shown below:

Column 24, line 40, change "memeber" to -- member --.

*Signed and Sealed this*

*Seventeenth* Day of *February 1981*

[SEAL]

*Attest:*

RENE D. TEGTMEYER

*Attesting Officer*    *Acting Commissioner of Patents and Trademarks*